United States Patent
Dai et al.

(10) Patent No.: US 11,618,872 B2
(45) Date of Patent: Apr. 4, 2023

(54) ANAEROBIC DIGESTION DEVICE BASED ON SELF-SUSTAINED AIR FLOTATION

(71) Applicant: TONGJI UNIVERSITY, Shanghai (CN)

(72) Inventors: Xiaohu Dai, Shanghai (CN); Yue Zhang, Shanghai (CN); Yu Hua, Shanghai (CN); Chen Cai, Shanghai (CN)

(73) Assignee: TONGJI UNIVERSITY, Shanghai (CN)

( * ) Notice: Subject to any disclaimer, the term of this patent is extended or adjusted under 35 U.S.C. 154(b) by 0 days.

(21) Appl. No.: 17/566,809

(22) Filed: Dec. 31, 2021

(65) Prior Publication Data

US 2022/0119746 A1   Apr. 21, 2022

Related U.S. Application Data

(63) Continuation of application No. PCT/CN2019/121601, filed on Nov. 28, 2019.

(30) Foreign Application Priority Data

Aug. 26, 2019   (CN) .......................... 201910789403.1

(51) Int. Cl.
  *C12M 1/107*   (2006.01)
  *C12M 1/00*   (2006.01)
  (Continued)

(52) U.S. Cl.
  CPC ............ *C12M 21/04* (2013.01); *C12M 23/34* (2013.01); *C12M 23/36* (2013.01); *C12M 23/56* (2013.01);
  (Continued)

(58) Field of Classification Search
  CPC ...... C12M 21/04; C12M 23/34; C12M 23/36; C12M 23/56; C12M 27/06; C12M 29/02;
  (Continued)

(56) References Cited

U.S. PATENT DOCUMENTS

2018/0320963 A1   11/2018   Baxter et al.

FOREIGN PATENT DOCUMENTS

| CN | 2515186 Y | 10/2002 |
|----|-----------|---------|
| CN | 101092268 A | 12/2007 |

(Continued)

OTHER PUBLICATIONS

Machine Translation of CN 101092268 from EPO; Accessed Jul. 30, 2022 (Year: 2022).*

(Continued)

*Primary Examiner* — William H. Beisner
*Assistant Examiner* — Danielle B Henkel

(57) ABSTRACT

An anaerobic digestion device based on self-sustained air flotation includes an anaerobic digestion tank unit, a self-sustained air flotation screening unit and a biogas measurement and collection unit. The self-sustained air flotation screening unit includes an air flotation screening part, a material sedimentation part, a reflux part and a three-phase separation part connected sequentially from bottom to top. A digested material in the anaerobic digestion tank unit is pumped into the air flotation screening part, overflows into the material sedimentation part, and then is raised to the reflux part. Gas passing through the three-phase separation part and gas produced in the anaerobic digestion tank unit enter the biogas measurement and collection unit to be measured and collected.

6 Claims, 3 Drawing Sheets

(51) Int. Cl.
*C12M 1/09* (2006.01)
*C12M 1/06* (2006.01)
*C12M 1/02* (2006.01)
*C12M 1/34* (2006.01)

(52) U.S. Cl.
CPC ............ *C12M 27/06* (2013.01); *C12M 29/02* (2013.01); *C12M 29/04* (2013.01); *C12M 29/26* (2013.01); *C12M 41/22* (2013.01); *C12M 41/26* (2013.01); *C12M 41/44* (2013.01); *C12M 47/10* (2013.01); *C12M 47/18* (2013.01)

(58) Field of Classification Search
CPC ...... C12M 29/04; C12M 29/26; C12M 41/22; C12M 41/26; C12M 41/44; C12M 47/10; C12M 47/18; C02F 1/24; C02F 1/001; C02F 2001/007; Y02E 50/30
See application file for complete search history.

(56) References Cited

FOREIGN PATENT DOCUMENTS

| | | |
|---|---|---|
| CN | 201339033 Y | 11/2009 |
| CN | 202508941 U | 10/2012 |
| CN | 103803770 A | 5/2014 |
| CN | 105886393 A | 8/2016 |
| CN | 205473795 U | 8/2016 |
| CN | 110468033 A | 11/2019 |
| GB | 2013646 A | 8/1979 |
| JP | H10202281 A | 8/1998 |
| JP | 2011092943 A | 5/2011 |
| WO | WO-2019102364 A1 * | 5/2019 |

OTHER PUBLICATIONS

Dennis A. Burke; Anaerobic Digestion of Sewage Sludge Using the Anoxic Gas Flotation (AGF) Process; Jan. 31, 1997; Cyclus Envirosystems, 6007 Hill Road NE, Olympia, WA 98516-9551.

Cristina Cagnetta, Bart Saerens, Francis A. Meerburg, Stijn O. Decru and Eddie Broeders . etc.; High-rate activated sludge systems combined with dissolved air flotationenable effective organics removal and recovery; Jul. 17, 2019; Center for Microbial Ecology and Technology (CMET), Ghent University, Coupure Links 653, Ghent 9000, Belgium.

Xiaohu Dai, Yu Hua, Huiping Li, Rui Liu, Shuxian Chen, Lingling Dai and Chen Cai; Coupling self-sustaining air flotation screening with conventional CSTR enhances anaerobic biodegradability of corn stover; Apr. 20, 2020; State Key Laboratory of Pollution Control and Resources Reuse, College of Environmental Science and Engineering, Tongji University, Shanghai 200092, China.

* cited by examiner

ANAEROBIC DIGESTION DEVICE BASED ON SELF-SUSTAINED AIR FLOTATION

CROSS-REFERENCE TO RELATED APPLICATIONS

This application is a continuation of International Patent Application No. PCT/CN2019/121601, filed on Nov. 28, 2019, which claims the benefit of priority from Chinese Patent Application No. 201910789403.1, filed on Aug. 26, 2019. The content of the aforementioned applications, including any intervening amendments thereto, is incorporated herein by reference in its entirety.

TECHNICAL FIELD

This application relates to anaerobic digestion of organic solid waste, and more particularly to an anaerobic digestion device based on self-sustained air flotation.

BACKGROUND

At present, the organic solid waste in China mainly comes from daily life (such as urban sludge, domestic garbage and garden waste), agricultural production (such as agricultural straw, mulch film and livestock and poultry manure) and industrial production (oil sludge, bacterial residue and industrial organic solids). The organic solid waste has an annual output of more than 6 billion tons, which accounts for more than 60% of the total solid waste generation. However, a scientific and reasonable management and safe disposal system has not yet been formulated. The organic solid waste, with typical pollution properties, has complex components and many harmful medias. The land-occupied storage of the organic solid waste will lead to a multi-phase combined cross-contamination with the surrounding environment, which is extremely complicated to control and causes mass incidents frequently. Therefore, the disposal of the organic solid waste has attracted considerable attention.

The recycling methods of the organic solid waste mainly include solidification, thermochemical conversion and anaerobic digestion. Regarding the anaerobic digestion, the organic solid waste is converted into $CH_4$, $CO_2$ or $H_2$ under the action of anaerobic microorganisms. Particularly, $CH_4$ has a high calorific value of 802.3 kJ/mol, and is accepted as an ideal energy material. By means of the anaerobic digestion, clean energy is produced while achieving the environment purification, and the digested residue can also be used as an organic fertilizer, providing benefits to energy, environmental protection and ecology. Therefore, the anaerobic digestion is a sustainable and environmentally friendly technology. In addition, the anaerobic digestion can also reduce waste odors and pathogens, and the digestion residues rich in the organic matter, plant nutrients and valuable nutrients can be reused.

With the emergence of the second-generation anaerobic reactor represented by the up-flow anaerobic sludge bed (UASB) and the third-generation anaerobic reactor represented by the expanded granular sludge bed (EGSB), the organic load rate (OLR) of the anaerobic treatment of sewage has increased to 50 kg $COD(m^3 \cdot d)^{-1}$ or even more than 100 kg $COD(m^3 \cdot d)^{-1}$. Anaerobic technology has made great achievements in the sewage treatment, and the anaerobic digestion theory is being completed. However, the application of anaerobic digestion in the treatment of organic solid waste is still limited. Due to the complex composition of the organic solid waste, the anaerobic fermentation is not easy to be conducted, and the existing reactors for the organic solid waste still need to be improved. With respect to lignocellulosic biomass, if the volumetric yield of the decomposition of the lignocellulosic biomass is represented by the measured production rate $(COD(V \cdot t)^{-1})$ of volatile fatty acid (VFA), the traditional anaerobic biogas digester only has a volumetric yield of 6 $g(L \cdot d)^{-1}$. A high-load anaerobic digestion process suitable for the organic solid waste is required to improve the anaerobic fermentation efficiency of organic solid waste. The ruminant digestive system is a naturally-occurring efficient anaerobic reactor, and has an organic load of 100 $kgDM(m^3 \cdot d)^{-1}$ and a VFA production rate per unit volume of about 18 $g(L \cdot d)^{-1}$, which are significantly superior to those of the traditional anaerobic reactor.

SUMMARY

An objective of the present disclosure is to provide an anaerobic digestion device based on self-sustained air flotation to overcome the shortcomings in the prior art, such as short-cut flow of undegraded substrate and lack of selectivity in discharging.

The technical solutions of the present disclosure are described as follows.

An anaerobic digestion device based on self-sustained air flotation, comprising:

an anaerobic digestion tank unit;

a self-sustained air flotation screening unit; and a biogas measurement and collection unit;

wherein the self-sustained air flotation screening unit is bidirectionally connected with the anaerobic digestion tank unit through a feeding pump and a reflux pump; and the biogas measurement and collection unit is connected to an air outlet of the self-sustained air flotation screening unit and an air outlet of the anaerobic digestion tank unit; and the self-sustained air flotation screening unit comprises an air flotation screening part, a material sedimentation part, a reflux part and a three-phase separation part connected sequentially from bottom to top; the air flotation screening part and the material sedimentation part are arranged side by side at a bottom of the self-sustained air flotation screening unit, and are separated through a central partition plate; a bottom of the air flotation screening part and a bottom of the material sedimentation part are both provided with a discharging port; the reflux part is arranged at a middle-upper part of the self-sustained air flotation screening unit; an upper end of the reflux part is higher than the air flotation screening part and the material sedimentation part; a lower end of the reflux part is connected to a reflux valve and is communicated with the reflux pump; a biogas outlet of the three-phase separation part is communicated with the biogas measurement and collection unit; a digested material in the anaerobic digestion tank unit is pumped from bottom to top to flow into the air flotation screening part through the feeding pump; after a liquid level in the air flotation screening part reaches a height of the central partition plate, the digested material overflows into the material sedimentation part; after a liquid level in the material sedimentation part reaches the height of the central partition plate, the digested material in the material sedimentation part is communicated with the digested material in the air flotation screening part; as the digested material is continuously fed to the self-sustained air flotation screening unit, the liquid level in the air flotation screening part and the liquid level in the material sedimentation part together rise to the upper end of the reflux part, and the digested material overflows into the reflux part;

the digested material collected in the reflux part is pumped back to the anaerobic digestion tank unit through the reflux pump; and gas passing through the three-phase separation part and gas produced in the anaerobic digestion tank unit enter the biogas measurement and collection unit.

In some embodiments, a height-to-diameter ratio of the air flotation screening part and a height-to-diameter ratio of the material sedimentation part are greater than or equal to 6.

In some embodiments, a diversion baffle plate or a gas diversion tube is arranged in the air flotation screening part and the material sedimentation part.

In some embodiments, a plurality of sampling valves are provided at different heights on a side of the air flotation screening part and a side of the material sedimentation part.

In some embodiments, the anaerobic digestion tank unit comprises a tank main body, a heating system and a stirring system; the stirring system is arranged at an inner center of the tank main body; the heating system is circumferentially arranged outside the tank main body; a side surface of the tank main body is provided with a circulating feeding port and a circulating discharging port; the circulating feeding port is communicated with a lower end of the air flotation screening part; the circulating discharging port is communicated with a lower end of the reflux part; a top of the tank main body is provided with a biogas outlet, a solid feeding inlet, an acid liquid inlet, an alkali liquid inlet, a pH or temperature detector and a stirring motor; and a discharging port is provided at a bottom of the tank main body.

In some embodiments, the heating system is a water-bath jacket heating system, a coil heating system or a combination thereof.

In some embodiments, the stirring system is a central axis stirring system, a horizontal stirring system, a side inclined stirring system or an internal submersible stirring system.

In some embodiments, a residence time of the digested material in the anaerobic digestion tank unit is 20-40 days.

In some embodiments, a residence time of the digested material in the self-sustained air flotation screening unit is 5-10 days.

In some embodiments, a temperature of the anaerobic digestion device is 35-39° C., 41-45° C. or 53-57° C.

In some embodiments, the biogas measurement and collection unit comprises a gas flow meter and a biogas collection device.

The beneficial effects of the present disclosure are described as follows.

Considering the phenomenon that the organic matter is degraded to produce biogas in the anaerobic digestion, the anaerobic digestion device provided herein is equipped with a self-supporting air flotation screening unit to optimize the structure, so as to achieve the self-sustained air flotation screening and recovery of the highly active microorganism and the discharge of the material hard to degrade, preventing the insufficient degradation in the anaerobic digestion due to the short flow of the material.

The anaerobic digestion device provided herein has simple structure and high degree of automation, and is convenient to operate and maintain. The device is suitable for a newly-designed project of organic solid waste anaerobic digestion and biogas production, and can also be used to optimize an established anaerobic digestion project, so as to realize the high-efficiency screening, hydrolysis and biogas production.

Figure 1:
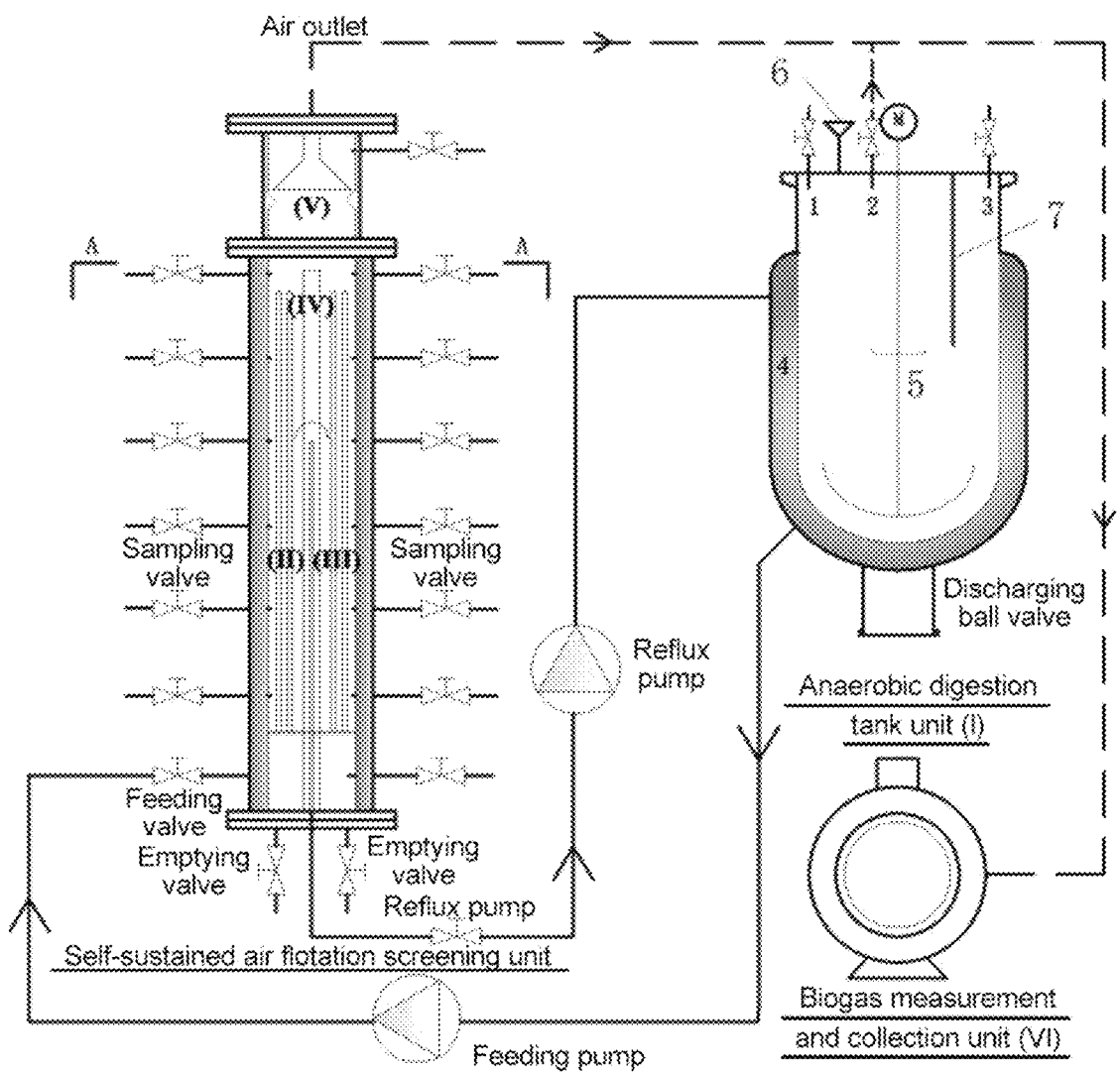
FIG. 1 schematically depicts a structure of an anaerobic digestion device based on a self-sustained air flotation according to an embodiment of the present disclosure.

In the drawings, I, anaerobic digestion tank unit; II, air flotation screening part; III, material sedimentation part; IV, reflux part; V, three-phase separation part; VI, biogas measurement and collection unit; 1, acid liquid inlet; 2, biogas outlet; 3, alkali liquid inlet; 4, heating system; 5, stirring system; 6, solid feeding inlet; 7, pH or temperature detector; and 8, stirring motor.

DETAILED DESCRIPTION OF EMBODIMENTS

An anaerobic digestion device with enhanced biogas production based on self-sustained air flotation is provided herein.

The anaerobic digestion device includes an anaerobic digestion tank unit I, a self-sustained air flotation screening unit and a biogas measurement and collection unit VI. The self-sustained air flotation screening unit is bidirectionally connected with the anaerobic digestion tank unit I through the feeding pump and a reflux pump. The biogas measurement and collection unit VI is connected to an air outlet of the self-sustained air flotation screening unit and an air outlet of the anaerobic digestion tank unit I.

The self-sustained air flotation screening unit includes an air flotation screening part II, a material sedimentation part III, a reflux part IV and a three-phase separation part V connected sequentially from bottom to top. The air flotation screening part II and the material sedimentation part III are arranged side by side at a bottom of the self-sustained air flotation screening unit, and are separated through a central partition plate. In some embodiments, the air flotation screening part II and the material sedimentation part III are respectively arranged in two tanks. A bottom of the air flotation screening part II and a bottom of the material sedimentation part III are both provided with a discharging port. The material sedimentation part III, replacing the anaerobic digestion tank unit I, discharges sludge regularly from the bottom of the material sedimentation part III. The reflux part IV is arranged at a middle-upper part of the self-sustained air flotation screening unit, and an upper end of the reflux part IV is higher than the air flotation screening part II and the material sedimentation part III, so as to ensure that a light active material in the air flotation screening part II and the material sedimentation part III overflows into the reflux part IV during an air flotation process. A lower end of the reflux part IV is connected to a reflux valve, and is communicated with the reflux pump. The three-phase separation part V is arranged at a top of the air flotation screening part II, the material sedimentation part III and the reflux part IV. If the air flotation screening part II and the material sedimentation part III are separately arranged, a top of the air flotation screening part II and a top of the material sedimentation part III are respectively provided with the three-phase separation part V. A biogas outlet of the three-phase separation part V is communicated with the biogas measurement and collection unit VI. A digested material in the anaerobic digestion tank unit I is pumped from bottom to top to flow into the air flotation screening part II through a feeding pump. After a liquid level in the air flotation screening part II reaches a height of the central partition plate, the digested material overflows into the material sedimentation part III. After a liquid level in the material sedimentation part III reaches the height of the central partition plate, the digested material in the material sedimentation part III is communicated with the digested material in the air flotation screening part II. As the digested material is continuously fed to the self-sustained air flotation screening unit, the liquid level in the air flotation screening part II and the liquid level in the material sedimentation part III together rise to the upper end of the reflux part IV, and the digested material overflows into the reflux part IV. The digested material collected in the reflux part IV is pumped back to the anaerobic digestion tank unit I through the reflux pump. Gas passing through the three-phase separation part V and gas produced in the anaerobic digestion tank unit I enter the biogas measurement and collection unit VI. The biogas measurement and collection unit VI includes a gas flow meter and a biogas collection device.

Specifically, a height-to-diameter ratio of the air flotation screening part II and a height-to-diameter ratio of the material sedimentation part III are greater than or equal to 6. A diversion baffle plate or a gas diversion tube is arranged in the air flotation screening part II and the material sedimentation part III to facilitate separation of the light active material and a heavy inert material during the air flotation process. A plurality of sampling valves are provided at different heights on a side of the air flotation screening part II and a side of the material sedimentation part III.

The anaerobic digestion tank unit I includes a tank main body, a heating system and a stirring system. The stirring system is arranged at an inner center of the tank main body. The heating system is circumferentially arranged outside the tank main body. A side surface of the tank main body is provided with a circulating feeding port and a circulating discharging port. The circulating feeding port is communicated with a lower end of the air flotation screening part II, and the circulating discharging port is communicated with a lower end of the reflux part IV, such that a light-weight and highly active microorganism screened by the air flotation screening part II and the material sedimentation part III fills up the reflux part IV, and then returns to the anaerobic digestion tank unit I through the reflux pump. A top of the tank main body is provided with a biogas outlet 2, a funnel-shaped solid feeding inlet 6, an acid liquid inlet 1, an alkali liquid inlet 3, a pH or temperature detector 7 (or adding an oxidation reduction potential (ORP) detector) and a stirring motor 8. The biogas outlet 2 is communicated with the biogas measurement and collection unit VI. A discharging port is provided at a bottom of the tank main body.

The heating system is a water-bath-jacket heating system or a coil heating system.

The stirring system is a central axis stirring system, a horizontal stirring system, a side inclined stirring system or an internal submersible stirring system.

A residence time of the digested material in the anaerobic digestion tank unit I is 20-40 days. A residence time of the digested material in the self-sustained air flotation screening unit is 5-10 days.

A temperature of the anaerobic digestion device is 35-39° C., 41-45° C. or 53-57° C.

The present disclosure will be further described below with reference to the embodiments.

EMBODIMENT

As shown in FIG. 1, an anaerobic digestion device with enhanced biogas production based on self-sustained air flotation provided herein includes an anaerobic digestion tank unit I using a continuous stirred tank reactor (CSTR) as an example, a self-sustained air flotation screening unit and a biogas measurement and collection unit VI. The self-sustained air flotation screening unit integrates four parts, which specifically includes an air flotation screening part II, a material sedimentation part III, a reflux part IV and a three-phase separation part V. A digested material in the anaerobic digestion tank unit I is selected from municipal sludge, and is pumped into the air flotation screening part II through a peristaltic feeding pump. A liquid level of the digested material in the air flotation screening part II rises over a central partition plate, and the digested material in the air flotation screening part II overflows into the material sedimentation part III. As the self-sustained air flotation screening unit continuously feeds the digested material, a light-weight and highly active microorganism screened by the air flotation screening part II and the material sedimentation part III is upgraded to the reflux part IV of a central cylinder, and then the screened highly active material is sent back to the anaerobic digestion tank unit I through a peristaltic reflux pump. Gas passing through the three-phase separation part V at a top of the air flotation screening part II, the material sedimentation part III and the reflux part IV and gas produced by the anaerobic digestion tank unit I enter the biogas measurement and collection unit VI taking a wet gas flowmeter as an example. The anaerobic digestion tank unit I and the self-sustained air flotation screening unit realize automatic control of various components through an electric control cabinet using a programmable-logic-controller (PLC) program, greatly reducing the difficulty of reactor operation and control. Both the anaerobic digestion tank unit I and the self-sustained air flotation screening unit are provided with an external water bath jacket, and internal heating of the anaerobic digestion device is realized through an external circulation of hot water.

Figure 2:
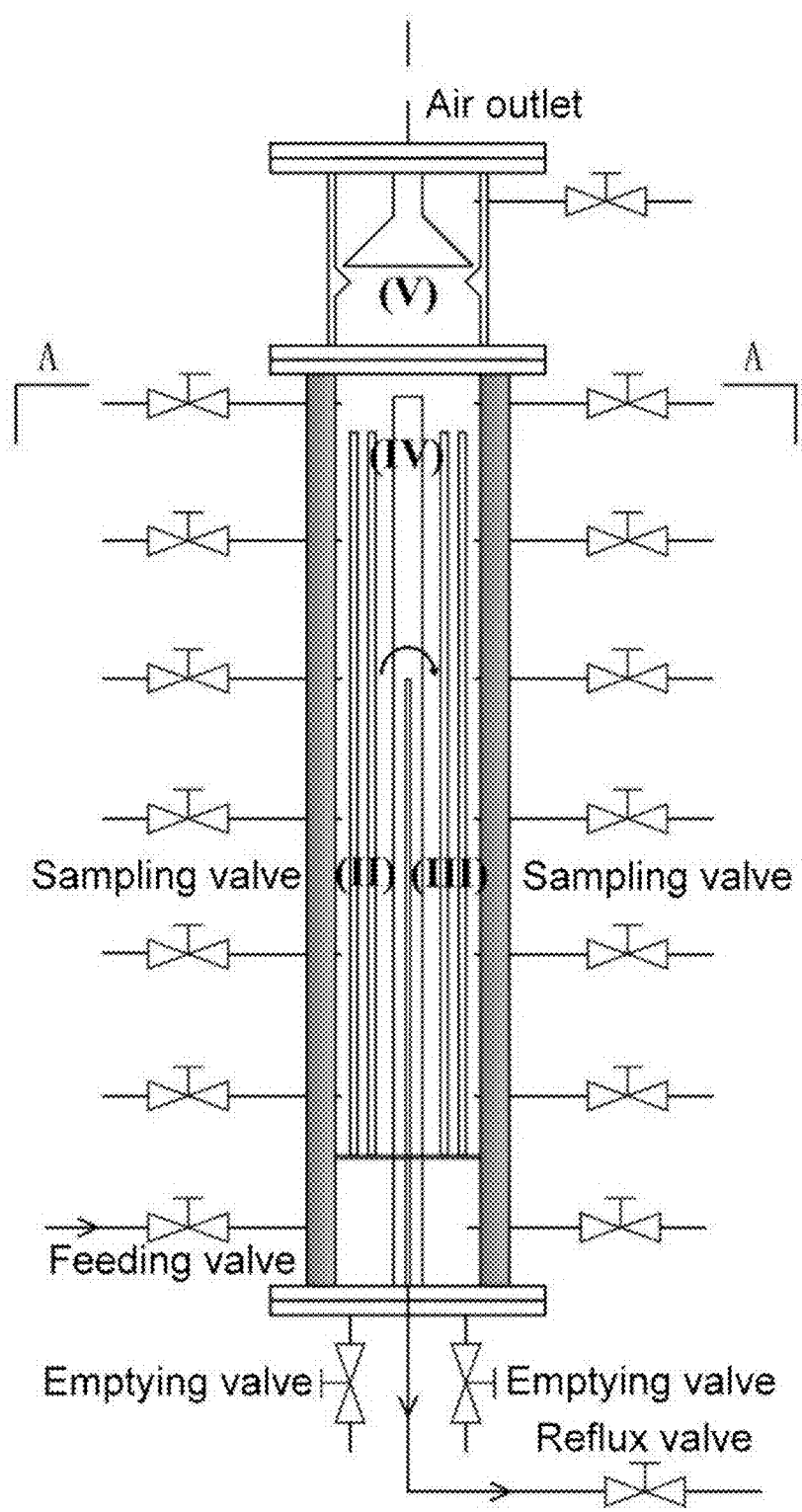
FIG. 2 is a longitudinal section view of a self-sustained air flotation screening unit along A-A in FIG. 1.

As shown in FIG. 2, the air flotation screening part II and the material sedimentation part III are arranged side by side at a bottom of the self-sustained air flotation screening unit and separated by the central partition plate, so as to facilitate separation of a light active material and a heavy inert material during an air flotation process. A height-to-diameter ratio of the air flotation screening part II and a height-to-diameter ratio of the material sedimentation part III are 6.5. A bottom of the air flotation screening part II and a bottom of the material sedimentation part III are both provided with a discharging port. The material sedimentation part III, replacing the anaerobic digestion tank unit I, discharges sludge every day from the bottom of the material sedimentation part III. The reflux part IV is arranged at a middle-upper part of the self-sustained air flotation screening unit, and an upper end of the reflux part IV is higher than the air flotation screening part II and the material sedimentation part III, so as to ensure that the light active material in the air flotation screening part II and the material sedimentation part III overflows into the reflux part IV during the air flotation process. The three-phase separation part V is arranged at a top of the air flotation screening part II, the material sedimentation part III and the reflux part IV. The biogas measurement and collection unit VI includes a gas flow meter and a biogas collection device.

Figure 3:
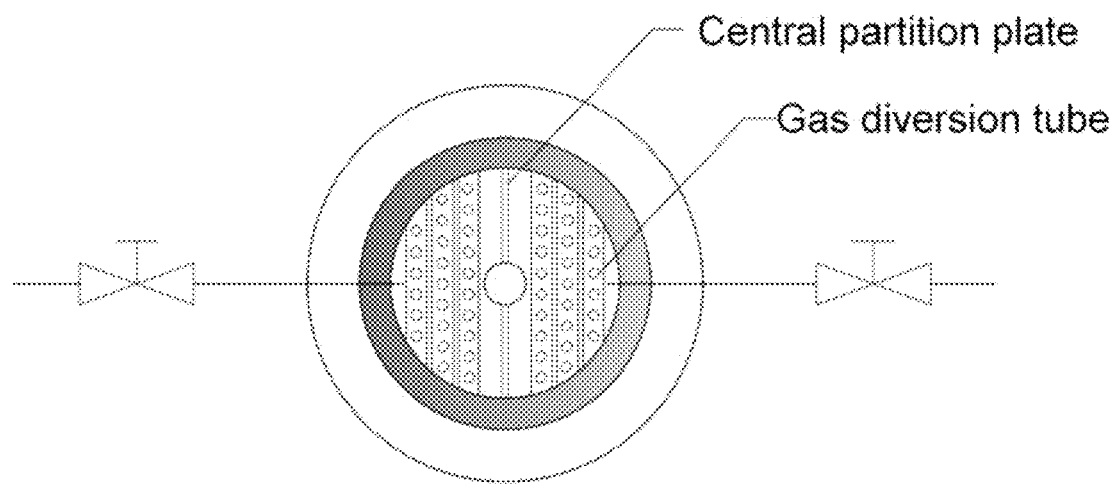
FIG. 3 is a cross-sectional view of the self-sustained air flotation screening unit according to an embodiment of the present disclosure.

As shown in FIG. 3, a gas diversion tube is arranged in the air flotation screening part II and the material sedimentation part III to facilitate the separation of the light active material and the heavy inert material during the air flotation process. A plurality of sampling valves are provided at different heights on a side of the air flotation screening part II and a side of the material sedimentation part III.

Figure 4:
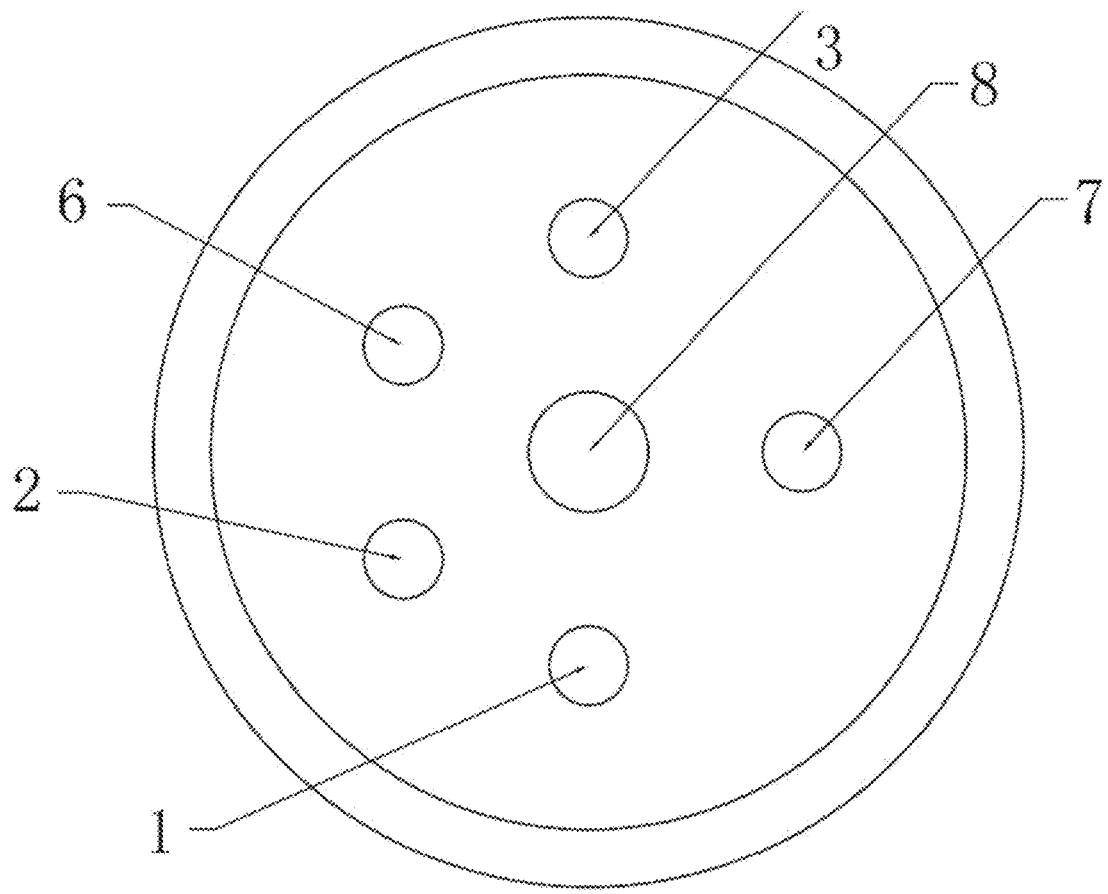
FIG. 4 is a top view of a tank main body in an anaerobic digestion tank unit according to an embodiment of the present disclosure.

As shown in FIGS. 1 and 4, the anaerobic digestion tank unit I includes a tank main body, a heating system and a stirring system. The stirring system is arranged at an inner center of the tank main body. The heating system is circumferentially arranged outside the tank main body. The stirring system provided herein is a central axis stirring system. A surface side of the tank main body is provided with a circulating feeding port and a circulating discharging port. The circulating feeding port is communicated with a lower end of the air flotation screening part II, and the circulating discharging port is communicated with a lower end of the reflux part IV, such that a light-weight and highly active microorganism screened by the air flotation screening part II and the material sedimentation part III fills up the reflux part IV, and then returns to the anaerobic digestion tank unit I through a reflux pump. A top of the tank main body is provided with a biogas outlet 2, a funnel-shaped solid feeding inlet 6, an acid liquid inlet 1, an alkali liquid inlet 3, a pH or temperature detector 7 (or adding an ORP detector) and a stirring motor 8. The sludge is replenished every day from the solid feeding inlet in a half-day continuous operation. The biogas outlet 2 is communicated with the biogas measurement and collection unit VI. A discharging port is provided at a bottom of the tank main body.

A temperature of the anaerobic digestion device is 37±1° C.

After more than 20 days of semi-continuous operation of methane production reaction, the biogas produced by the anaerobic digestion tank unit I and the self-sustained air flotation screening unit is collected and measured by the biogas measurement and collection unit VI taking a wet gas flowmeter as an example. Compared with the conventional CSTR anaerobic reactor, the anaerobic digestion device provided herein effectively increases the gas production per unit organic matter in sludge by 20-30%.

The embodiments mentioned above are merely illustrative to facilitate the understanding and use of the present disclosure. It should be noted that modifications and applications made by those skilled in the art without departing from the spirit of this disclosure should fall within the scope of the present disclosure defined by the appended claims.

What is claimed is:

1. An anaerobic digestion device based on self-sustained air flotation, comprising:
    an anaerobic digestion tank;
    a self-sustained air flotation screening unit; and
    a biogas collector equipped with a gas flow meter;
    wherein the self-sustained air flotation screening unit is bidirectionally connected with the anaerobic digestion tank through a feeding pump and a reflux pump; and the biogas collector is connected to an air outlet of the self-sustained air flotation screening unit and an air outlet of the anaerobic digestion tank; and
    the self-sustained air flotation screening unit comprises an air flotation screening part, a material sedimentation part, a reflux part and a three-phase separation part connected sequentially from bottom to top; the air flotation screening part and the material sedimentation part are arranged side by side at a bottom of the self-sustained air flotation screening unit and are separated through a central partition plate; a bottom of the air flotation screening part and a bottom of the material sedimentation part are both provided with a discharging port; the reflux part is arranged at a middle-upper part of the self-sustained air flotation screening unit; an upper end of the reflux part is higher than the air flotation screening part and the material sedimentation part; a lower end of the reflux part is connected to a reflux valve and is communicated with the reflux pump; a biogas outlet of the three-phase separation part is communicated with the biogas collector; a digested material in the anaerobic digestion tank is pumped from bottom to top to flow into the air flotation screening part through the feeding pump; after a liquid level in the air flotation screening part reaches a height of the central partition plate, the digested material overflows into the material sedimentation part; after a liquid level in the material sedimentation part reaches the height of the central partition plate, the digested material in the material sedimentation part is communicated with the digested material in the air flotation screening part; as the digested material is continuously fed to the self-sustained air flotation screening unit, the liquid level in the air flotation screening part and the liquid level in the material sedimentation part together rise to the upper end of the reflux part, and the digested material overflows into the reflux part; the digested material collected in the reflux part is pumped back to the anaerobic digestion tank through the reflux pump; and gas passing through the three-phase separation part and gas produced in the anaerobic digestion tank enter the biogas collector.

2. The anaerobic digestion device of claim 1, wherein a height-to-diameter ratio of the air flotation screening part and a height-to-diameter ratio of the material sedimentation part are greater than or equal to 6.

3. The anaerobic digestion device of claim 1, wherein a diversion baffle plate or a gas diversion tube is arranged in the air flotation screening part and the material sedimentation part; and/or
    a plurality of sampling valves are provided at different heights on a side of the air flotation screening part and a side of the material sedimentation part.

4. The anaerobic digestion device of claim 1, wherein the anaerobic digestion tank comprises a tank main body, a heating system and a stirring system; the stirring system is arranged at an inner center of the tank main body; and the heating system is circumferentially arranged outside the tank main body;
    a side surface of the tank main body is provided with a circulating feeding port and a circulating discharging port; the circulating feeding port is communicated with a lower end of the air flotation screening part; the circulating discharging port is communicated with a lower end of the reflux part; a top of the tank main body is provided with a biogas outlet, a solid feeding inlet, an acid liquid inlet, an alkali liquid inlet, a pH or temperature detector and a stirring motor; and a discharging port is provided at a bottom of the tank main body.

5. The anaerobic digestion device of claim 4, wherein the heating system is a water-bath-jacket heating system or a coil heating system.

6. The anaerobic digestion device of claim 4, wherein the stirring system is a central axis stirring system, a horizontal stirring system, a side inclined stirring system or an internal submersible stirring system.

* * * * *